US009267921B2

(12) United States Patent
Michaeu-Cunningham et al.

(10) Patent No.: US 9,267,921 B2
(45) Date of Patent: Feb. 23, 2016

(54) AXIAL AND CIRCUMFERENTIAL FLAW SENSING EDDY CURRENT PROBE

(75) Inventors: Jevne Branden Michaeu-Cunningham, Seattle, WA (US); Anil Sood, Bellevue, WA (US); Steve Timm, Bellevue, WA (US); William Ziegenhagen, Kent, WA (US); Pauline Tarango, Renton, WA (US)

(73) Assignee: Zetec, Inc., Snoqualmie, WA (US)

( * ) Notice: Subject to any disclaimer, the term of this patent is extended or adjusted under 35 U.S.C. 154(b) by 192 days.

(21) Appl. No.: 13/537,649

(22) Filed: Jun. 29, 2012

(65) Prior Publication Data

US 2014/0002070 A1    Jan. 2, 2014

(51) Int. Cl.
*G01N 27/90* (2006.01)

(52) U.S. Cl.
CPC .......... *G01N 27/902* (2013.01); *G01N 27/9033* (2013.01)

(58) Field of Classification Search
CPC ............................... G01N 27/90; G01N 27/82
See application file for complete search history.

(56) References Cited

U.S. PATENT DOCUMENTS

| 3,876,831 | A | * | 4/1975 | Wickham et al. | 178/20.04 |
| 5,881,310 | A | * | 3/1999 | Airhart et al. | 710/3 |
| 6,150,809 | A | * | 11/2000 | Tiernan et al. | 324/238 |
| 7,381,483 | B2 | * | 6/2008 | Cheng et al. | 428/843.7 |
| 8,436,608 | B2 | * | 5/2013 | Sun et al. | 324/240 |
| 8,466,674 | B2 | * | 6/2013 | Suzuma et al. | 324/240 |
| 2004/0066191 | A1 | * | 4/2004 | Hils et al. | 324/257 |
| 2011/0241665 | A1 | * | 10/2011 | Takatsuji | 324/253 |

FOREIGN PATENT DOCUMENTS

| DE | 4412042 A1 * | 10/1995 | ............. G01N 27/90 |
| FR | 2780509 A1 | 12/1999 | |
| JP | 2009069090 A | 4/2009 | |

OTHER PUBLICATIONS

T.E. Capobianco, "Rotating field eddy current probe for characterization of cracking in non-magnetic tubing", Jul. 31, 1998, XP055078018, New York, Retrieved from the Internet: URL:http://www.osti.gov/bridge/servlets/purl/353191-V8oWIK/webviewable/353191.pdf [retrieved on Sep. 6, 2013].

Oka M et al, "Non-Destructive Testing on Stainless Steel Plate by Rotational Magnetic Flux Sensor", IEEE Transactions on Magnetics, IEEE Service Center, New York, NY, US, vol. 33, No. 5, Sep. 1, 1997, pp. 3373-3375, XP011031699, ISSN: 0018-9464, DOI: 10.1109/20.617948 paragraph [0002]; figure 1b.

(Continued)

*Primary Examiner* — Tung X Nguyen
*Assistant Examiner* — Feba Pothen
(74) *Attorney, Agent, or Firm* — Caesar Rivise, PC

(57) ABSTRACT

A rotating field eddy current probe for sensing flaws in electrically conductive tubing is disclosed. The probe includes two stimulation coils physically arranged at 90 degrees to each other about an axis a current sensing portion. The a first alternating current is applied to one of the stimulation coils at a first phase and a second alternating current is applied to the second of the stimulation coils at a second phase, said second phase being electrically 90 degrees apart from said first phase and creating a rotating oscillating magnetic field.

16 Claims, 1 Drawing Sheet

(56) References Cited

OTHER PUBLICATIONS

Junjun Xin et al, "Nondestructive Inspection Using Rotating Magnetic Field Eddy-Current Probe", IEEE Transactions on Magnetics, IEEE Service Center, New York, NY, US, vol. 47, No. 5, May 1, 2011, pp. 1070-1073, XP011354304, ISSN: 0018-9464, DOI: 10.1109/TMAG.2011.2108996 paragraph [0002].

International Search Report mailed Sep. 13, 2013 for PCT/US2013/047839.

* cited by examiner

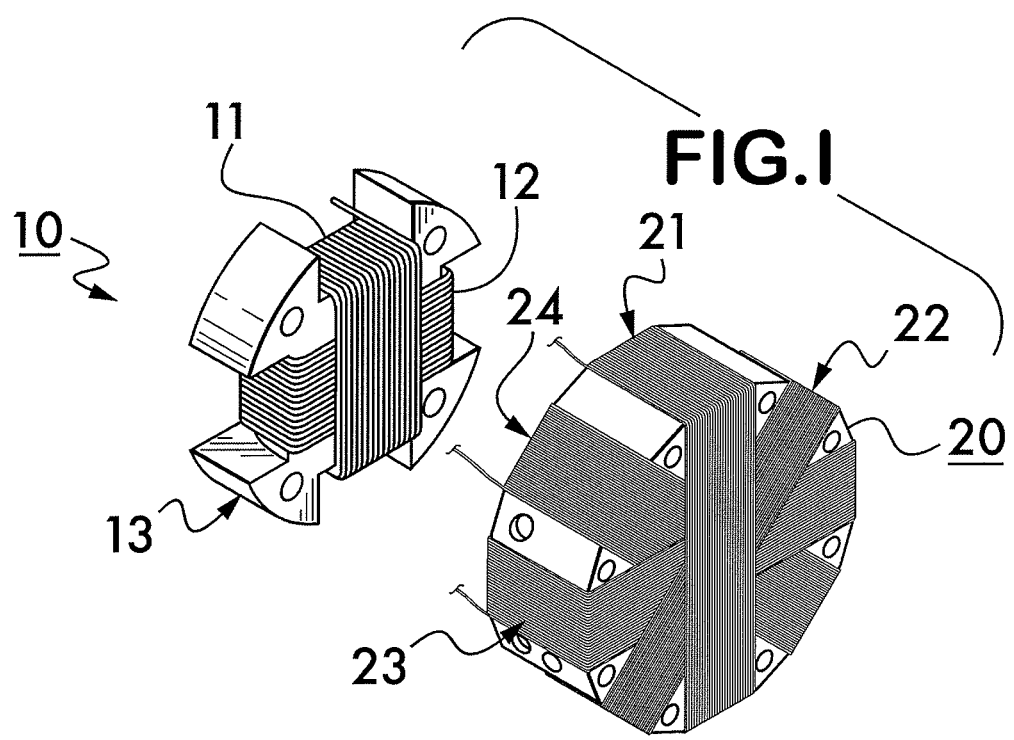
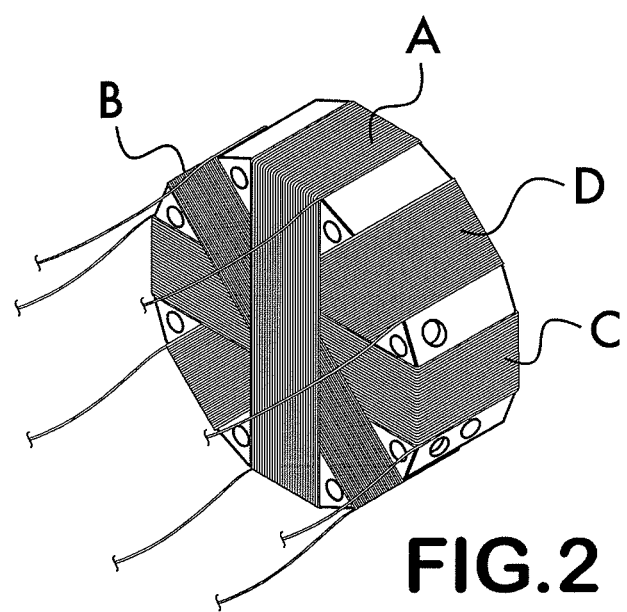

AXIAL AND CIRCUMFERENTIAL FLAW SENSING EDDY CURRENT PROBE

BACKGROUND OF THE INVENTION

1. Field of Invention

The present invention relates to eddy current monitoring and in particular a probe for eddy current monitoring of boiler tubes.

2. Description of Related Art

The process of testing metal for failure with eddy current probes is well known in the art. Further, the use of this technology in the field of boiler tube testing is also well known. Within the non-destructive inspection industry, clearly identifying and classifying mater anomalies is critical to reliability and safety of the devices under inspection. The identification of characteristics such as fatigue cracks, stress corrosion cracking (SCC), intra-granular attack (IGA), pitting, fretting and other material or dimensional profile changes can have a catastrophic effect on material or part integrity.

Traditional eddy current testing (ECT) has been the dominant tool for studying the integrity of conductive materials. The most predominant type of ECT probe is the bobbin probe. Due to the geometry of the stimulating coil and the resultant eddy current field morphology, a bobbin probe has far higher probability of detection for axial flaws than circumferential flaws.

Current systems use complex multi-inductive coil probes with application specific integrated circuit drive electronics mounted at the probe head to interface with the coils to perform multiplexing. This arrangement allows a full inspection of axial and circumferential flaws, but requires that power be supplied to the sensor head for the electronics. The need for power at the head and associated electronics can negatively impact reliability due to delivery induced electrical failures and device failures.

There remains a need for a simple probe for sensing both axial and circumferential tube flaws that does not require a powered head.

All references cited herein are incorporated herein by reference in their entireties.

BRIEF SUMMARY OF THE INVENTION

In an embodiment of the invention, there is disclosed a rotating field eddy current probe for sensing flaws in electrically conductive tubing. The probe includes two stimulation coils physically arranged at 90 degrees to each other about an axis through the center of the stimulation coils and a current sensing portion. A first alternating current is applied to one of the stimulation coils at a first phase and a second alternating current is applied to the second stimulation coil at a second phase so that the second phase is electrically 90 degrees apart from the first phase. In an embodiment, the current sensing portion includes at least a first pair of detection coils physically arranged at 90 degrees to each other about a central axis. The current sensing portion also comprises a second pair of coils arranged at 90 degrees to each other and at 45 degrees to the first two pair of detection coils.

In alternate embodiments the current sensing portion of the probe has an Anisotropic Magneto-Resistance sensor, a Giant Magneto-Resistance sensor, a Giant Magneto-Impedance sensor or a planar inductor sensor.

In an alternate embodiment the current sensing portion comprises a ring of search-coil inductive sensing elements.

In alternate embodiments, the current sensing portion is operated in one of the following modes: absolute passive sensing mode, differential passive sensing mode, absolute impedance mode, or differential impedance mode.

In a further embodiment, the stimulation coils are not energized and one pair of detection coils is energized and the second pair of detection coils senses magnetic fields.

In an embodiment, the stimulation coils are wound on a ferrite core.

In an embodiment the current sensing portion coils are wound on a polymer core having a magnetic permeability substantially equal to 1. In further embodiments, the current sensing portion coils are wound on a core containing a high magnetic permeability selected from the group consisting of ferrite, mu-metal or permalloy-80.

BRIEF DESCRIPTION OF SEVERAL VIEWS OF THE DRAWINGS

The invention will be described in conjunction with the following drawings in which like reference numerals designate like elements and wherein:

FIG. 1 is a drawing of exemplary stimulation and reception coils in an exemplary rotating field eddy current probe for tube inspection.

FIG. 2 is a drawing of an exemplary four coil assembly.

DETAILED DESCRIPTION OF THE INVENTION

In an exemplary embodiment, the inventive probe, comprises two coil assemblies as shown in FIG. 1. The stimulation coil assembly 10 has windings 11 and 12, which are positioned at 90 degrees to each other and wound on a ferrite core 13. The second coil assembly 20 can be used for sensing fields created by flaws, but in addition, because the second coil assembly includes several windings on a polymer core with a low magnetic permeability 21, 22, 23, and 24, the second coil assembly can also be used to both stimulate the subject material and sense any resultant fields created due to flaws. The second coil assembly can also be used for impedance-mode sensing measurements, as well as transmit-receive pairs both by using single coils and with differential pairing of windings. Note that the probe is passive in that there are no powered electronic components located in the probe head. Drive circuitry is remote from the probe head.

Coil assembly 20 includes four windings, equally spaced around the core.

In an embodiment, the stimulation orthogonal windings 11 and 12 are energized with a sinusoidal current such that one winding 11 is at a first phase and the second winding 12 is energized at 90 degrees to the phase of the first winding 11. This creates a reciprocating time varying eddy current vector field that sweeps 360 degrees in the plane 110 of the area under test 100 about any point in the plane of the area under test. This creates a rotating oscillating magnetic field. The effect of this rotating field is to induce eddy currents that will, at some point, align themselves orthogonally with any circumferential and/or axial flaw. Stimulation in this orientation leads to the maximum magnetic flux leakage to be sensed where there is a flaw. Any magnetic flux leakage in the tube under inspection is sensed by the windings in the second coil assembly 20. These windings are arranged to have preferred sense directions oriented to highly discriminate circumferential flaws and their location.

The applicants have learned that having directional receive elements simplifies the use of rotating field technology. Because of the volume of data that can be extracted from a rotating field eddy current probe at the frequencies of inspection, it is necessary to correlate sensed signal to eddy current field direction. Extracting 360 degrees worth of information can be a difficult computing challenge in the absence of additional information that is available with a directionally oriented sensor such as is disclosed herein. Intelligent discrimination at the sensor by alignment of the dominant sensing axis orthogonally to the indication of interest minimizes the amount of processing needed to analyze the data.

The second coil assembly 20 includes two sets of mutually perpendicular coils. Each individual coil is wound such that there is a preferred coupling direction if the individual filament in each coil to circumferential indications. This uniaxial sensing element is purposely designed to give directional discrimination to the time varying rotating field driven flux leakage due to a flaw.

The two sets of coils can be operated in the following modes: absolute passive sensing, where each coil serves as a single sensor; differential passive sensing, where two coils positioned at 90 degrees to each other are used in a differential mode; absolute impedance mode where the impedance of a single coil is measured; differential impedance mode where the impedance of two coils at 90 degrees is measured; and co-radial transmit-receive pairs, where two of the coil sets are energized and the remaining two are uses as sensors. In this mode, the energized coils are at 90 degrees to each other and the receive coils are at 90 degrees to each other. With reference to FIG. 2 an example is that coils A and C are energized and coils B and D are the receive coils.

In a further embodiment, the second coil assembly when used in a sensing mode is replaced with and one of the following known sensor technologies and used in conjunction with the rotating oscillating filed generated by the first coil assembly. The substitute sensors for the second coil assembly include Anisotropic Magneto-Resistance (AMR), Giant Magneto-Resistance (GMR), Giant Magneto-Impedance (GMI), laser-etched inductive sensors and planar inductors (both unidirectional and omnidirectional).

In a further embodiment the sensing portion of the device is an array ring of inductive sensing elements oriented around the circumference of the probe for tube inner-diameter inspection.

Each of the above-described probe configurations can also be used for tube profilometry in addition to flaw detection.

While the invention has been described in detail and with reference to specific examples thereof, it will be apparent to one skilled in the art that various changes and modifications can be made therein without departing from the spirit and scope thereof.

What is claimed is:

1. A rotating field eddy current probe for sensing flaws in electrically conductive tubing having a circular cross section comprising:
    two stimulation coils wound about a first common bobbin and physically arranged at 90 degrees to each other about an axis through the center of said stimulation coils and said first common bobbin, said bobbin being arranged such that said axis is aligned longitudinally with the tubing and
    a current sensing portion;
    wherein a first alternating current is applied to the first of said stimulation coils at a first phase and a second alternating current is applied to the second of said stimulation coils at a second phase, said second phase being electrically 90 degrees apart from said first phase, said first and second alternating currents configured to induce eddy currents in said tubing wherein said current sensing portion comprises at least a first pair of detection coils wound about a second common bobbin and physically arranged at 90 degrees to each other about said axis and configured to sense a rotating field produced by said eddy currents induced in the tubing.

2. The probe of claim 1, wherein said current sensing portion comprises a second pair of coils wound on said second common bobbin and arranged at 90 degrees to each other and at 45 degrees to said first two pair of detection coils.

3. A rotating field eddy current probe for sensing flaws in electrically conductive tubing having a circular cross section comprising:
    two stimulation coils wound about a first common bobbin and physically arranged at 90 degrees to each other about an axis through the center of said stimulation coils and said first common bobbin being arranged such that said axis is aligned longitudinally with the tubing and
    a current sensing portion;
    wherein a first alternating current is applied to the first of said stimulation coils at a first phase and a second alternating current is applied to the second of said stimulation coils at a second phase, said second phase being electrically 90 degrees apart from said first phase, said first and second alternating currents configured to induce eddy currents in said tubing wherein said current sensing portion comprises:
    at least a first and second pair of magnetic flux detectors, each pair placed opposite each other about said axis and not coplanar with said stimulation coils and wherein said first and second pairs are arranged at 90 degrees to each other about said axis and configured to sense a rotating field produced by said eddy currents induced in the tubing.

4. The probe of claim 3, wherein said current sensing portion comprises a Giant Magneto-Resistance sensor.

5. The probe of claim 3, wherein said current sensing portion comprises an Giant Magneto-Impedance sensor.

6. The probe of claim 3, wherein said current sensing portion comprises a planar inductor.

7. The probe of claim 3, wherein said current sensing portion comprises a ring of search-coil inductive sensing elements.

8. The probe of claim 1, wherein said current sensing portion is operated in an absolute passive sensing mode.

9. The probe of claim 1, wherein said current sensing portion is operated in a differential passive sensing mode.

10. The probe of claim 1, wherein said current sensing portion is operated in an absolute impedance mode.

11. The probe of claim 1, wherein said current sensing portion is operated in a differential impedance mode.

12. The probe of claim 1, wherein said stimulation coils are not energized and said first pair of detection coils is energized and said second pair of coils senses magnetic fields.

13. The probe of claim 1, wherein said stimulation coils are wound on a ferrite core.

14. The probe of claim 1, wherein said current sensing portion coils are wound on a polymer core having a magnetic permeability substantially equal to 1.

15. The probe of claim 1, wherein said current sensing portion coils are wound on a core containing a high magnetic permeability selected from the group consisting of ferrite, mu-metal or permalloy-80.

16. The probe of claim 3, wherein said current sensing portion comprises an Anisotropic Magneto-Resistance sensor.

* * * * *